US008389753B2

(12) United States Patent
Higgins et al.

(10) Patent No.: US 8,389,753 B2
(45) Date of Patent: Mar. 5, 2013

(54) STABILIZED VEGETABLE OILS AND METHODS OF MAKING SAME

(75) Inventors: Neil Wallace Higgins, Bourbonnais, IL (US); Jerry F. Stults, Ostrander, OH (US)

(73) Assignee: Bunge Oils, Inc., St. Louis, MO (US)

( * ) Notice: Subject to any disclaimer, the term of this patent is extended or adjusted under 35 U.S.C. 154(b) by 901 days.

(21) Appl. No.: 12/371,804

(22) Filed: Feb. 16, 2009

(65) Prior Publication Data

US 2009/0205535 A1    Aug. 20, 2009

Related U.S. Application Data

(63) Continuation-in-part of application No. 12/032,472, filed on Feb. 15, 2008, now abandoned.

(60) Provisional application No. 61/030,095, filed on Feb. 20, 2008, provisional application No. 61/031,866, filed on Feb. 27, 2008.

(51) Int. Cl.
    *C07C 67/00*    (2006.01)
(52) U.S. Cl. ....................................................... 554/124
(58) Field of Classification Search .................... 554/124
    See application file for complete search history.

(56) References Cited

U.S. PATENT DOCUMENTS

| 4,011,239 A | 3/1977 | Heiba et al. |
| 4,014,910 A | 3/1977 | De Klein |
| 4,119,646 A * | 10/1978 | Heiba et al. .................... 549/462 |
| 4,158,741 A | 6/1979 | Goi et al. |
| 4,175,089 A * | 11/1979 | Heiba et al. .................... 549/326 |
| 4,285,868 A | 8/1981 | Heiba et al. |
| 4,328,363 A | 5/1982 | Heiba et al. |
| 4,380,650 A | 4/1983 | Coleman et al. |
| 4,736,063 A | 4/1988 | Coleman et al. |
| 4,739,014 A | 4/1988 | Parks et al. |
| 4,806,447 A | 2/1989 | Parker |
| 5,945,489 A | 8/1999 | Moy et al. |
| 6,201,143 B1 | 3/2001 | O'Lenick, Jr. |
| 6,201,144 B1 | 3/2001 | Isbell et al. |
| 6,316,649 B1 | 11/2001 | Cermack et al. |
| 6,583,302 B1 | 6/2003 | Erhan et al. |

OTHER PUBLICATIONS

International Preliminary Report on Patentability corresponding to International Patent Application Serial No. PCT/US2007/076093, mailed Feb. 26, 2009.
Guner, "Anchovy Oil Thermal Polymerization Kinetics", Istanbul Technical University, Chemical Engineering Department, Turkey, J. Am. Oil. Chem. Soc., vol. 74, No. 12 (1997).
Aichholz et al. High Temperature Gas Chromatography and High Temperature Gas Chromatography-Negaitve Chemical Ionization Mass Spectrometry of Derivated Triglycerides containing Oxygenate Fatty Acid Acyl Groups, J. High Resolution Chromatography, Mar. 1998, vol. 21, pp. 152-160.
Becamel, Phiippe, Notification Concerning Transmittal of International Preliminary Report on Patentability (Chapter I of the Patent Cooperation Treaty (PCT Rule 44bis.1(c)), and International Preliminary Report on Patentability, corresponding to International Patent Application Serial N. PCT/US2007/076093, mailed Feb. 26, 2009.

(Continued)

*Primary Examiner* — Deborah D Carr
(74) *Attorney, Agent, or Firm* — Jones Day

(57) ABSTRACT

A method for modifying ethylenic unsaturation in a triglyceride. One or more unsaturated fatty acyl moieties present in the triglyceride are substituted with a a lactone substitution, a dihydrofuran substitution, or a ketone substitution via an electron acceptor mediated reaction. The resulting reaction products are useful, for example, as lubricants, metalworking fluids, mold release agents, hydraulic fluids, or dielectric fluids, or as components of lubricants, metalworking fluids, mold release agents, hydraulic fluids, or dielectric fluids, and modified fatty acids for polymer synthesis.

30 Claims, 3 Drawing Sheets

OTHER PUBLICATIONS

Figure 1:
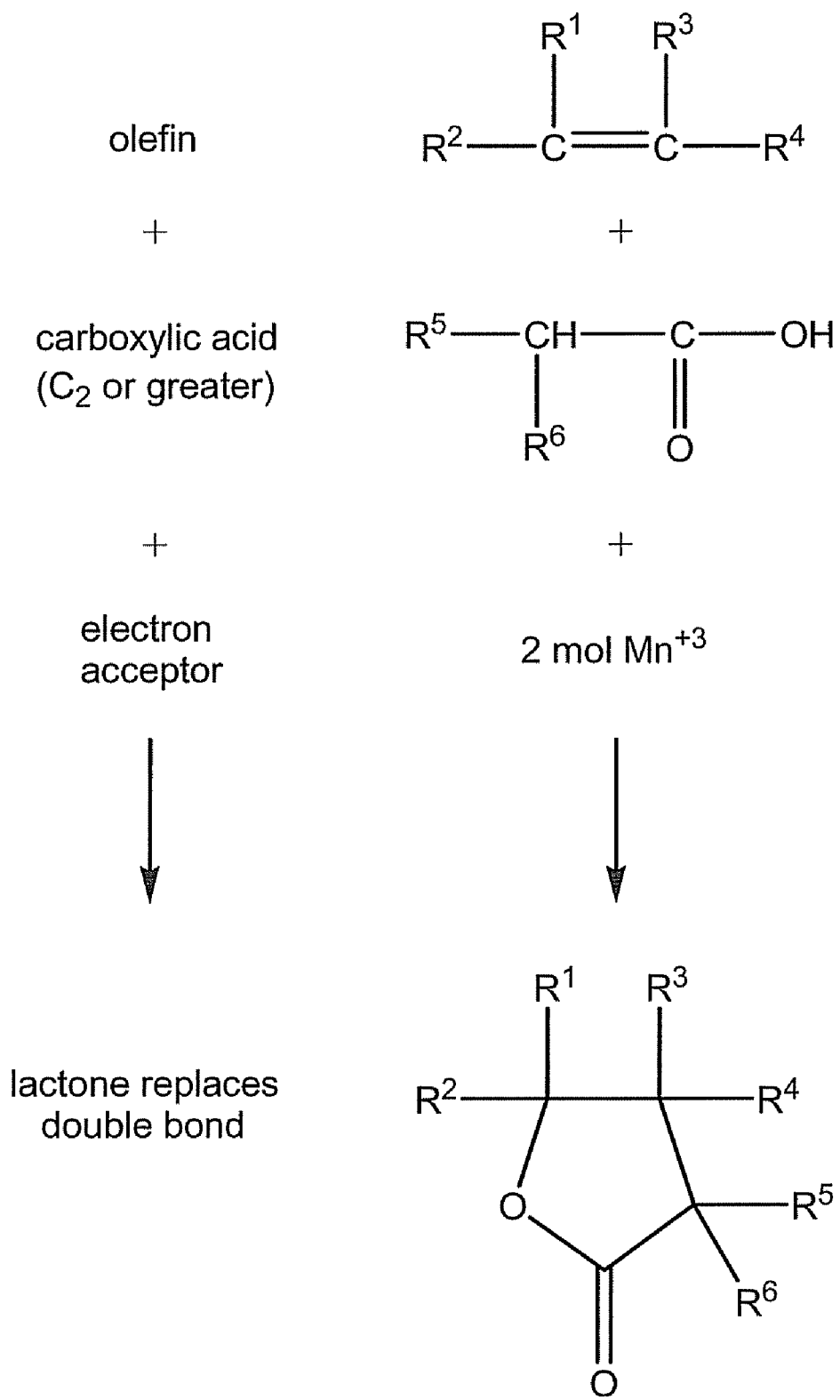

Biermann, Ursela, et al., New Syntheses With Oils and Fata as Renewable Raw Materials for the Chemical Industry, in Biorefineries—Industrial Processes and Products: Status Quo and Future Directions, vol. 2 (Birgit Kamm, Patrick R. Gruber & Michael Kamm eds., 2006).

Carr, Deborah D., Non-Final Office Action, corresponding to U.S. Appl. No. 11/839,853, mailed Jun. 27, 2008, 12 pages.

Carr, Deborah D., Notice of Allowance and Fee(s) Due, corresponding to U.S. Appl. No. 11/839,853, mailed Jan. 5, 2009, 4 pages.

Carr, Deborah D., Non-Final Office Action, corresponding to U.S. Appl. No. 12/032,472, mailed Mar. 24, 2010, 10 pages.

Carr, Deborah D., Non-Final Office Action, corresponding to U.S. Appl. No. 12/240,676, mailed Sep. 17, 2009.

De La Mare, Harold E., Kochi, Jay K. and Rust, Frederick F., Oxidation and Reduction of Free Radicals by Metal Salts, J. Amer. Chem. Soc., May 20, 1963, pt. 1437-1449.

Demir, Ayhan S. and Emrullahoglu, Mustafa, Manganese(III) Acetate: A Versatile Reagent in Organic Chemistry, Curr. Org. Syn., 2007, 4, p. 223-237.

Eyler, Yvonne, Notification of Transmittal of the International Search Report and The Written Opinion of the International Searching Authority, or the Declaration, corresponding to International Application No. PCT/US2007/76093, mailed Jan. 25, 2008, 5 pages.

Eyler, Yvonne, Written Opinion of the International Searching Authority, corresponding to International Application No. PCT/US2007/76093, mailed Jan. 25, 2008, 7 pages.

Heiba, E.I. and Dessau, R.M., Oxidation by Metal Salts, VII, Synthesis Based on the Selective Oxidation of Organic Free Radicals, J. Amer. Chem. Soc., 93:2 Jan. 27, 1971, p. 524-527.

Heiba, E.I. and Dessau, R.M., Oxidation by Metal Salts, VIII, The Decomposition of Ceric Carboxylates in The Presence of Olefins and Aromatic Hydrocarbons, J. Amer. Chem. Soc., 93:4 Feb. 24, 1971, p. 995-999.

Heiba, E.I. and Dessau, R.M., Oxidation by Metal Salts, X, One-Step Synthesis of Lactones From Olefins, J. Amer. Chem. Soc., 96:26 Dec. 25, 1974, p. 7977-7981.

Heiba, E.I. and Dessau, R.M., Williams, AL.L, Rodewald, P.G., Substituted Gamma Butyrolactones From Carboxylic Acids and Olefins: Gamma-(n-octyl)_gamma_butyrolactone, Organic Syntheses, Coll. vol. 7, p. 400 (1990), vol. 61, p. 22 (1983).

Kirk, Raymond E. and Othmer, Donald F., Encyclopedia of Chemical Technology, 4th Ed., vol. 10, pg. 254, 1972.

Onopchenko, Anatoni and Schultz, Johann G.D., Oxidation by Metal Salts, J. Org. Chem, vol. 57, No. 15, 1972, p. 2564-2566.

Snider, Barry B., Manganese(III)-Based Oxidative Free Radical Cyclizations, Chem. Rev. 1996, 96, 339-363.

Steenhorst-Slikkerveer et al. Analysis of Nonvolatile Lipid Oxidation Products in Vegetable Oils by Normal-Phase High-Performance Liquid Chromatograpy with Mass Spectrometric Detection, JAOCS, 2000, vol. 77, No. 8, pp. 837-845.

* cited by examiner

STABILIZED VEGETABLE OILS AND METHODS OF MAKING SAME

CROSS-REFERENCE TO RELATED APPLICATIONS

This is a continuation-in-part of U.S. Ser. No. 12/032,472, filed Feb. 15, 2008, now pending; this specification also claims the priority of U.S. Ser. No. 61/030,095, filed Feb. 20, 2008, and U.S. Ser. No. 61/031,866, filed Feb. 27, 2008. Each patent specification mentioned in this paragraph is incorporated here by reference.

Other related matters are U.S. Ser. No. 60/822,617, filed Aug. 16, 2006; U.S. Ser. No. 11/839,853, filed Aug. 16, 2007; and U.S. Ser. No. 12/240,676, filed Sep. 29, 2008, which are incorporated here by reference.

BACKGROUND OF THE INVENTION

The present invention relates to unsaturated fatty acyl moieties of free fatty acids, glycerides and other esters, in which sites of ethylenic unsaturation are stabilized via conversion to other moieties, including lactone, ketone, dihydrofuran, and vinyl groups. Compounds that are, or include, partial or complete lactone, ketone, dihydrofuran, or vinyl analogs of fatty acyl moieties are also contemplated, in which lactone, ketone, dihydrofuran, or vinyl moieties are linked into or pendant from a hydrocarbon chain.

Vegetable oils have some characteristics that favor their use as, or as a component in, lubricant formulations, hydraulic fluid formulations, and dielectric fluid formulations, including dielectric cooling fluid formulations. The long chain fatty acid and ester functionality of vegetable oils gives them good characteristics with respect to lubricity. They also have good resistance to passing electrical currents (dielectric strength). Their biodegradability and status as a renewable feedstock also give them advantages over petroleum-based products.

Vegetable oils, however, have shortcomings that have limited their use in lubricants, hydraulic fluids, and dielectric fluids, including dielectric cooling fluids. Vegetable oils have relatively low oxidative stability and relatively high pour points. Vegetable oils also tend to solidify when held at their pour points, unlike petroleum-based products. The oxidative stability problem is due to sites of ethylenic unsaturation (i.e. C=C bonds) in the hydrocarbon chains of fatty acyl moieties (i.e. RC(O)—, where R is an ethylenically unsaturated hydrocarbon moiety) of vegetable oils, with fatty acyl moieties containing more than one ethylenic double bond being particularly prone to oxidation.

These shortcomings have been addressed in many ways, such as additive packages containing antioxidants and pour point depressants and the use of synthetic esters, poly alpha olefins or other compounds as diluents to improve pour point.

The oxidative stability problem has been more directly addressed by partial hydrogenation to reduce the number of ethylenic double bonds, partial polymerization (heat bodying), breeding or artificial genetic modification of the oil-producing plants to increase the level of monounsaturated fatty acids in the oil, or hydroxylation followed by esterification of short chain fatty acids to the free hydroxyl groups (U.S. Pat. No. 6,583,302 B1 Erhan et al). Esters have been made with fatty acids and on the fatty acid chains of hydroxylated fatty acids (U.S. Pat. No. 6,316,649 B1 Cennack et al). In addition some work has been done with the formation of secondary ethers (U.S. Pat. No. 6,201,144 B1 Isbell et al). Free radical chemistry has been used to graft antioxidants into rubber (U.S. Pat. No. 4,739,014 Parks et al).

U.S. Pat. No. 4,011,239 (Heiba, et al) discloses selective reactions of free radicals with olefins in the presence of an ion of Mn, V, or Ce.

U.S. Pat. No. 6,201,143 B1 teaches making a polymer using meadowfoam oil fatty acids or meadowfoam oil as a starting material to form monomers with fatty acids with vinyl groups and making a polymer out of them. That patent mentions that the resulting polymer has enhanced oxidative stability.

Other documents possibly of interest include U.S. Pat. No. 4,014,910 (de Klein); U.S. Pat. No. 4,119,646 (Heiba, et al.); U.S. Pat. No. 4,175,089 (Heiba, et al.); U.S. Pat. No. 4,328,363 (Heiba, et al.); U.S. Pat. No. 4,736,063 (Coleman, et al.); U.S. Pat. No. 4,380,650 (Coleman, et al.); U.S. Pat. No. 4,158,741 (Goi, et al.); U.S. Pat. No. 6,201,143 B1; Anatoli Onopchenko and Johannn G. D. Schulz, *Oxidation by Metal Salts*, J. ORG. CHEM., Vol. 57, No. 16, 1972 pg 2564-2566; Harold E. De La Mare, Jay K. Kochi and Frederick F. Rust, *Oxidation and Reduction of Free Radicals by Metal Salts*, J. AMER. CHEM. SOC., May 20, 1963, Pg. 1437-1449; E. I. Heiba and R. M. Dessau, *Oxidation by Metal Salts. VIII. The Decomposition Of Ceric Carboxylates In The Presence Of Olefins And Aromatic Hydrocarbons*, J. AMER. CHEM. SOC., 93:4 Feb. 24, 1971 p. 995-999; E. I. Heiba, R. M. Dessau and P. G. Rodewald, *Oxidation by Metal Salts. X One-Step Synthesis Of (Gamma) Lactones From Olefins*, J. AMER. CHEM. SOC., 96:26 Dec. 25, 1974 pg 7977-7981; Barry B. Snider, *Manganese(III)-Based Oxidative Free Radical Cyclizations*, CHEM. REV. 1996, 96, 339-363; I. E. Heiba, R. M. Dessau, A. L. Williams; P. G. Rodewald, *Substituted Gamma Butyrolactones From Carboxylic Acids And Olefins: Gamma-(n-octyl)-gamma-butyrolactone*, ORGANIC SYNTHESES, COLL. Vol. 7, p 400 (1990) Vol. 61, p. 22 (1983) and Ursula Biermann et al., *New Syntheses with Oils and Fats as Renewable Raw Materials for the Chemical Industry*, in BIOREFINERIES—INDUSTRIAL PROCESSES AND PRODUCTS: STATUS QUO AND FUTURE DIRECTIONS, Vol. 2 (Birgit Kamm, Patrick R. Gruber & Michael Kamm eds., 2006).

All the above patents and publications are incorporated by reference in their entirety.

SUMMARY OF THE INVENTION

An aspect of the invention is a triglyceride having the structure:

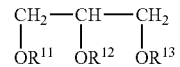

in which $R^{11}$, $R^{12}$, and $R^{13}$ are independently fatty acyl moieties, and at least one fatty acyl moiety of the triglyceride has a dihydrofuran substitution.

Another aspect of the invention is a method for modifying ethylenic unsaturation in a triglyceride. The starting triglyceride can have the following structure and fatty acyl moieties:

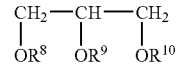

with the restriction that at least one of $R^8$, $R^9$, and $R^{10}$ is an ethylenically unsaturated fatty acyl moiety having at least one site of unsaturation available for dihydrofuran substitution. The triglyceride can be reacted with a ketone in the presence of manganese (III) acetylacetonate, forming a fused dihydrofuran on said at least one site of unsaturation.

Another aspect of the invention is a metalworking fluid comprising a triglyceride dispersed in an aqueous or non-aqueous carrier phase. The triglyceride has the structure:

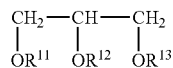

in which $R^{11}$, $R^{12}$, and $R^{13}$ are independently fatty acyl moieties. At least one fatty acyl moiety of the triglyceride has a lactone substitution, a ketone substitution, or a dihydrofuran substitution (or two or more of these).

Another aspect of the invention is a mold release agent comprising a triglyceride dispersed in an aqueous or non-aqueous carrier phase. The triglyceride has the structure and fatty acyl moieties shown above. At least one fatty acyl moiety of the triglyceride has a lactone substitution, a ketone substitution, or a dihydrofuran substitution (or two or more of these). As used in this disclosure, a reacting "ketone" may be either a cyclic ketone (i.e. the carbonyl carbon is a member of the ring) or an acyclic ketone (all other ketones), in different embodiments.

Another aspect of the invention is a method for modifying ethylenic unsaturation in a triglyceride. The triglyceride has the structure and fatty acyl moieties shown above, with the restriction that at least one of $R^8$, $R^9$, and $R^{10}$ is an ethylenically unsaturated fatty acyl moiety having at least one site of unsaturation available for lactone, ketone, or dihydrofuran substitution. The triglyceride can be reacted with a carboxylic acid having at least two carbon atoms in the presence of manganese (III) acetylacetonate, forming a lactone on said at least one site of unsaturation. Alternatively or in addition, the triglyceride can be reacted with a ketone in the presence of manganese (III) acetylacetonate, forming a ketone substituent or a dihydrofuran substituent on said at least one site of unsaturation.

BRIEF DESCRIPTION OF DRAWING FIGURES

FIG. 1 shows a reaction of an olefin with a carboxylic acid having two or more carbon atoms to form an analog of the olefin having a lactone ring in place of a site of ethylenic unsaturation in a fatty acid. The assignment in the product of "R" moieties of the reactants is contemplated to be correct, but the invention is not limited according to the accuracy of these assignments.

Figure 2:
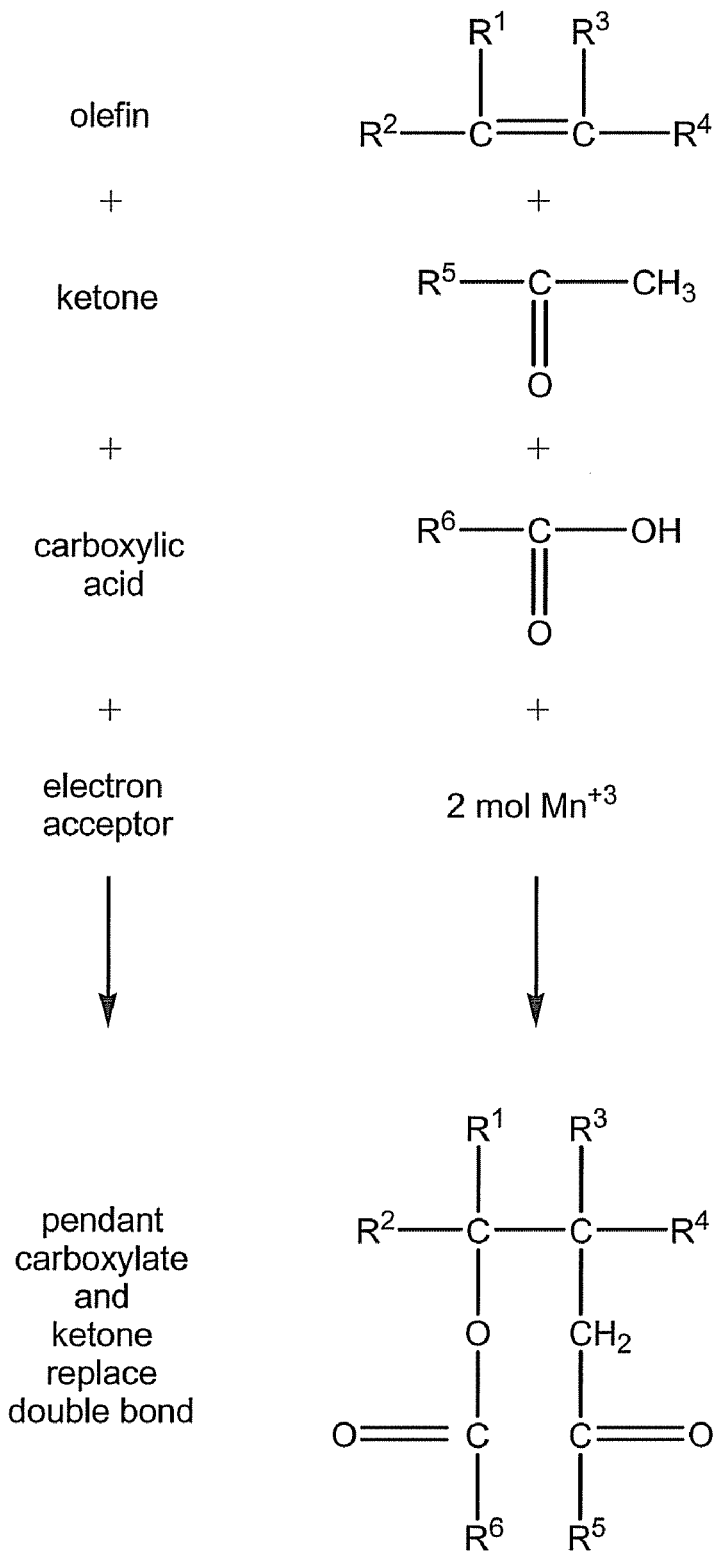

FIG. 2 shows a reaction of an olefin with a ketone moiety and a carboxylic acid to form an analog of the olefin having a pendant ketone group and a pendant carboxylate group in place of a site of ethylenic unsaturation in the fatty acid. A methyl ketone is shown as a reactant, but the analogous reaction is also contemplated with an independently selected $R^5$ moiety (limited to non-hetero-substituted alkyl moieties) in place of the methyl moiety as illustrated. The assignment in the product of "R" moieties of the reactants is contemplated to be correct, but the invention is not limited according to the accuracy of these assignments.

Figure 3:
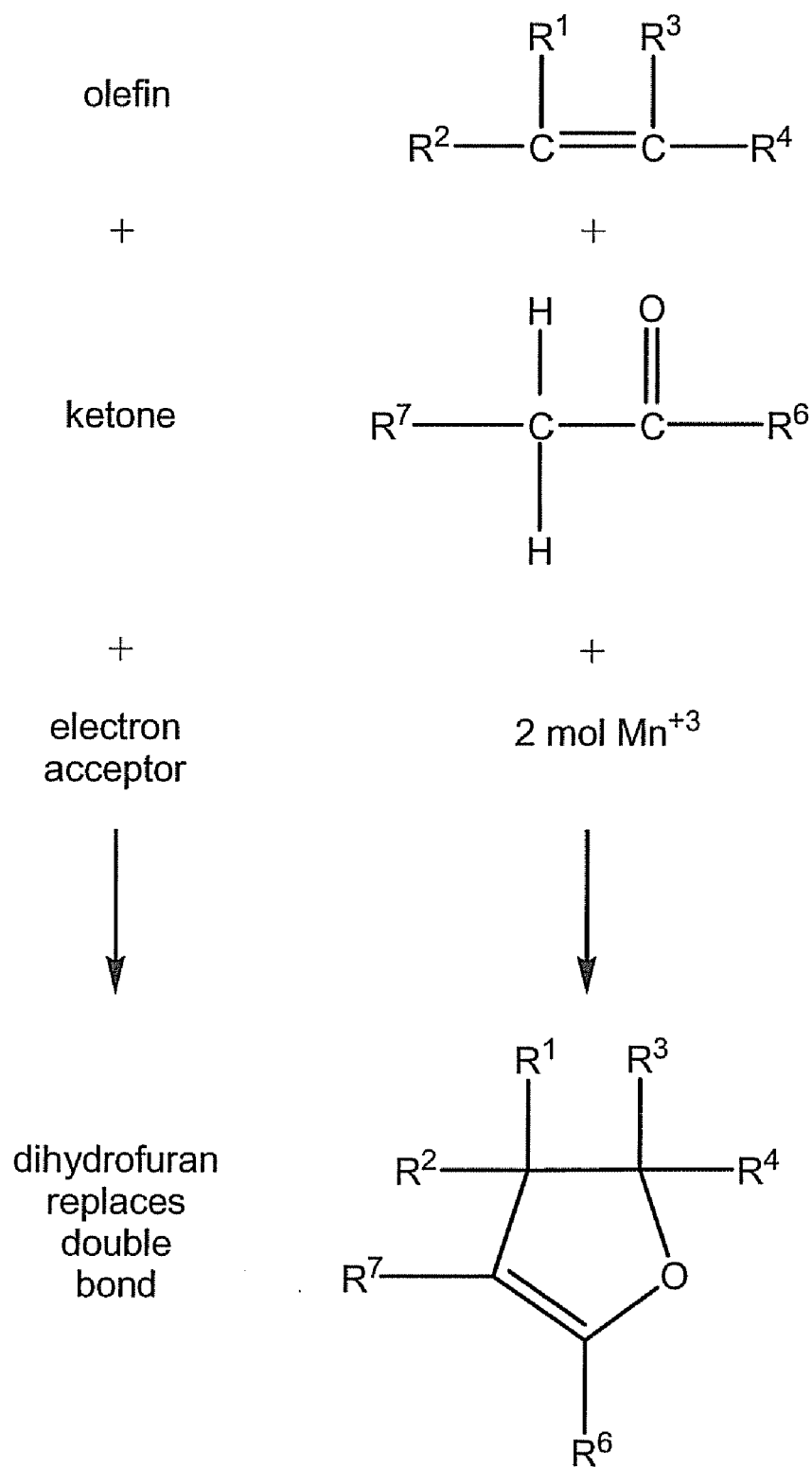

FIG. 3 shows a reaction of an olefin with a ketone reactant moiety, without necessarily using a carboxylic acid, to form an analog of the olefin having a fused dihydrofuran group in place of a site of ethylenic unsaturation in the hydrocarbon chain of a fatty acid or acyl moiety. The assignment in the product of "R" moieties of the reactants in the product is contemplated to be correct, but the invention is not limited according to the accuracy of these assignments.

DETAILED DESCRIPTION OF THE INVENTION

Certain embodiments provide a method for modifying unsaturated vegetable oils to improved certain properties, such as oxidative stability. Certain embodiments include vegetable oils modified with lactone, ketone, dihydrofuran, or vinyl moieties and having improved oxidative stability over the unmodified oil. Sites of ethylenic unsaturation in vegetable oils are prone to oxidative degradation. These same sites will preferentially react via free radical chemistry as compared to saturated sites in vegetable oils. Without being bound by a particular theory, it is contemplated that unsaturated sites separated by a methylene group are more oxidatively reactive than isolated unsaturated sites. Certain embodiments take advantage of the preferential reactivity present in the unsaturated fatty acyl moieties of vegetable oils to improve the oxidative stability of those vegetable oils.

In certain embodiments, a lactone structure is contemplated having the final structure of FIG. 1, in which a lactone moiety is substituted for at least one, alternatively two, alternatively three, alternatively four, alternatively five, alternatively six, alternatively all, of the ethylenic double bonds on at least one fatty acid chain. (The term "lactone" in this specification necessarily refers to a lactone nucleus with one or more R substituents as defined in this specification and FIG. 1.)

In this disclosure and FIGS. 1-3, $R^1$ and $R^3$ can be, for example, independently hydrogen, methyl, ethyl, n-propyl, i-propyl, n-butyl, i-butyl, or t-butyl. At least one of $R^2$ and $R^4$ can be, for example, a straight or branched acyl moiety having predominantly from 1-22 carbon atoms, alternatively predominantly from 4-20 carbon atoms, alternatively predominantly from 6-18 carbon atoms, alternatively predominantly from 12-14 carbon atoms, with a hydroxyl or ester terminal group (where R is a hydrocarbon). The other of $R^2$ and $R^4$ can be an acyl moiety with a hydroxyl terminal group or ester linkage as just described or hydrogen. $R^5$, $R^6$, and $R^7$ can be independently any of the previously mentioned alternatives for $R^1$-$R^4$. $R^7$ can also be joined to the nucleus by a carbonyl linkage, defining a diketone reactant.

Alternatively, lactone compounds made by any process and having the formula set forth as the final structure of FIG. 1 are contemplated.

Alternatively, an embodiment according to the bottom structure in FIG. 1 is contemplated which is the partial or complete lactone analog or product of the olefin or fatty acid defined by the beginning structure of FIG. 1. In this embodiment, the olefin at the top of FIG. 1 is alternatively palmitoleic acid, oleic acid, linoleic acid, linolenic acid, alpha-eleostearic acid, ricinoleic acid, gadoleic acid, arachidonic acid, cetoleic acid, erucic acid, or any of the unsaturated acids shown. in KIRK-OTHMER, ENCYCLOPEDIA OF SCIENCE AND TECHNOLOGY, 4th Ed., Vol. 10, page 254, which is incorporated by reference, or any combination of two or more of these. The lactone may be oriented as illustrated or in a flipped orientation in which $R^1$ and $R^3$ are switched and $R^2$ and $R^4$ are switched. A lactone moiety can be substituted for one, alternatively two, alternatively three, alternatively four, alternatively five, alternatively six, alternatively all, of the ethylenic double bonds on a fatty acid chain.

Alternatively, the free fatty acid chain of FIG. 1 can be a fatty acyl moiety of an ester, for example an alkyl ($C_{1-22}$, straight or branched chain) ester or a monoglyceride, diglyceride, or triglyceride ester. If the ester is a diglyceride ester, one of the fatty acid chains is lactone-modified and the other fatty acid chain is either lactone-modified or not. If the ester is a triglyceride ester, one of the fatty acid chains is lactone-modified and the other two are not, or two of the fatty acid chains are lactone-modified and the other one is not, or all three of the fatty acid chains are lactone-modified. Mixtures of two or more of these species are also contemplated.

In an embodiment, soybean oil or another vegetable oil or glyceride ester may be modified by substitution of a lactone ring for one, two, or three ethylenic double bonds per fatty acyl moiety, analogous to the illustrations in FIG. 1. For example, a linolenic acyl moiety of a soybean oil triglyceride (which is unsaturated at the 9, 12, and 15 positions) can be modified by converting the ethylenic double bond at the 15 position to a lactone ring, as shown in FIG. 1. Either that mono-substituted linolenic acyl or linoleic acyl, either of which has ethylenic unsaturation at the 9 and 12 positions, can be reacted as shown in FIG. 1 by converting the ethylenic double bond at the 12 position to a lactone ring. Either that di-substituted linolenic acyl, that monosubstituted linoleic acyl, or oleic acyl, any of which has ethylenic unsaturation at the 9 position, can be reacted as shown in FIG. 1 by converting the ethylenic double bond at the 9 position to a lactone ring, leaving a saturated acyl moiety with one, two, or three lactone rings, respectively.

An unsaturated free fatty acid or acyl moiety has been modified to reduce the amount of unsaturation by reacting an ethylenic double bond to produce a lactone structure on the fatty acid chain. Such lactone structures on fatty acid chains have been successfully produced using both a fatty acid mixture that is mainly oleic acid and soybean oil as starting materials. Analysis of the reacted fatty acid mixture or with the reacted soybean oil shows that the fatty acid composition as determined by gas chromatography (GC) analysis of methyl esters has changed compared to the starting material. It is contemplated that this change includes reformation of an ethylenic double bond as a linked-in lactone ring in the hydrocarbon chain of the acyl moiety.

It is also contemplated to modify any unsaturated free fatty acid by conversion of some or all of its ethylenic double bonds to lactone rings, and then make esters with the lactone modified fatty acids to gain the benefits of this approach to stabilizing triglycerides or esters to oxidation.

It is also contemplated to modify any unsaturated fatty acyl moiety of a triglyceride by conversion of some or all of its ethylenic double bonds to lactone rings, and then trans-esterify the triglycerides to gain the benefits of this approach to stabilizing triglycerides or esters to reduce oxidation.

It is further contemplated to prepare a lactone analog of any lubricant species containing ethylenic unsaturation, either by reacting the lubricant species directly or by reacting a precursor having ethylenic unsaturation as described here with a carboxylic acid as described here in the presence of a metal ion or other electron acceptor.

In certain embodiments, a structure is contemplated having the final structure of FIG. 2 or FIG. 3, in which a ketone reactant moiety, and in the case of FIG. 2 also a carboxylate moiety, are substituted for at least one, alternatively two, alternatively three, alternatively four, alternatively five, alternatively six, alternatively all, of the ethylenic double bonds on at least one fatty acid chain.

One sub-genus of reaction products of such ketones is pendant acyclic ketones made by any process and having the formula set forth as the final structure of FIG. 2. A methyl ketone is shown as a reactant in FIG. 2, producing a product with a methylene linkage in the pendant ketone, but the analogous reaction is also contemplated with an independently selected $R^5$ moiety (limited to non-hetero-substituted alkyl moieties) in place of the methyl moiety as illustrated, producing a corresponding $R^5$ alkylene moiety in the pendant ketone.

An embodiment according to the final structure in FIG. 2 is contemplated which is the partial or complete ketone analog or product of the olefin or fatty acid defined by the beginning structure of FIG. 2. In this embodiment, the olefin at the top of FIG. 2 is alternatively palmitoleic acid, oleic acid, linoleic acid, linolenic acid, alpha-eleostearic acid, ricinoleic acid, gadoleic acid, arachidonic acid, cetoleic acid, erucic acid, or any of the unsaturated acids shown in KIRK-OTHMER, ENCYCLOPEDIA OF SCIENCE AND TECHNOLOGY, $4^{th}$ Ed., Vol. 10, page 254, which is incorporated by reference, or any combination of two or more of these. The ketone may be oriented as illustrated or in a flipped orientation in which $R^1$ and $R^3$ are switched and $R^2$ and $R^4$ are switched. A ketone moiety and a carboxylate moiety can be substituted for one, alternatively two, alternatively three, alternatively four, alternatively five, alternatively six, alternatively all, of the ethylenic double bonds on a fatty acid chain.

Alternatively, the free fatty acid chains of FIG. 2 can be fatty acyl moieties of an ester, for example an alkyl ($C_{1-22}$, straight or branched chain) ester or a monoglyceride, diglyceride, or triglyceride ester. If the ester is a diglyceride ester, one of the fatty acid chains is ketone-modified and the other fatty acid chain is either ketone-modified or not. If the ester is a triglyceride ester, one of the fatty acid chains is ketone-modified and the other two are not, or two of the fatty acid chains are ketone-modified and the other one is not, or all three of the fatty acid chains are ketone-modified. Mixtures of two or more of these species are also contemplated.

In an embodiment, soybean oil or another vegetable oil or glyceride ester may be modified by substitution of an acyclic pendant ketone for one, two, or three ethylenic double bonds per fatty acyl moiety, analogous to the illustrations in FIG. 2. For example, a linolenic acyl moiety of a soybean oil triglyceride (which is unsaturated at the 9, 12, and 15 positions) can be modified by converting the ethylenic double bond at the 15 position to an acyclic pendant ketone, as shown in FIG. 2. Either that mono-substituted linolenic acyl or linoleic acyl, either of which has ethylenic unsaturation at the 9 and 12 positions, can be reacted as shown in FIG. 2 by converting the ethylenic double bond at the 12 position to an acyclic pendant ketone moiety and a carboxylate moiety. Either that di-ketone-substituted linolenic acyl, that monosubstituted linoleic acyl, or oleic acyl, any of which has ethylenic unsaturation at the 9 position, can be reacted as shown in FIG. 2 by converting the ethylenic double bond at the 9 position to an acyclic pendant ketone, leaving a saturated acyl moiety with one, two, or three ketone moieties, respectively.

Another sub-genus of such reaction products of ketones is fused rings made by any process and having the formula set forth as the final structure of FIG. 3. In certain embodiments, a dihydrofuran ring is formed, as illustrated in FIG. 3. (The term "dihydrofuran" in this specification necessarily refers to a dihydrofuran nucleus with one or more R substituents as defined in this specification and FIG. 3.) In other embodiments, in which $R^7$ includes a carbonyl linkage, a ketone structure is contemplated having the final structure of FIG. 3, in which a dihydrofuran moiety is substituted for at least one, alternatively two, alternatively three, alternatively four, alternatively five, alternatively six, alternatively all, of the ethylenic double bonds on at least one fatty acid chain. Another category within this subgenus is a ketone-substituted dihydrofuran, made by reacting a diketone according to the reaction of FIG. 3. For example, pentane-2,4-dione, reacted as shown in FIG. 3, is contemplated to yield the dihydrofuran product of FIG. 3, in which $R^7$ is a methylcarbonyl moiety.

An embodiment according to the final structure in FIG. 3 is contemplated which is the partial or complete ketone or ring-modified analog or product of the olefin or fatty acid defined by the beginning structure of FIG. 3. In this embodiment, the olefin at the top of FIG. 3 is alternatively palmitoleic acid, oleic acid, linoleic acid, linolenic acid, alpha-eleostearic acid, ricinoleic acid, gadoleic acid, arachidonic acid, cetoleic acid, erucic acid, or any of the unsaturated acids shown in KIRK-OTHMER, ENCYCLOPEDIA OF SCIENCE AND TECHNOLOGY, $4^{th}$ Ed., Vol. 10, page 254, which is incorporated by reference, or any combination of two or more of these. The dihydrofuran substituted product may be oriented as illustrated or in a flipped orientation in which $R^1$ and $R^3$ are switched and $R^2$ and $R^4$ are switched. A dihydrofuran ring can be substituted for one, alternatively two, alternatively three, alternatively four, alternatively five, alternatively six, alternatively all, of the ethylenic double bonds on a fatty acid chain.

Alternatively, the free fatty acid chains of FIG. 3 can be fatty acyl moieties of an ester, for example an alkyl ($C_{1-22}$, straight or branched chain) ester or a monoglyceride, diglyceride, or triglyceride ester. If the ester is a diglyceride ester, one of the fatty acid chains is dihydrofuran-modified and the other fatty acid chain is either dihydrofuran-modified or not. If the ester is a triglyceride ester, one of the fatty acid chains is dihydrofuran-modified and the other two are not, or two of the fatty acid chains are dihydrofuran-modified and the other one is not, or all three of the fatty acid chains are dihydrofuran-modified. Mixtures of two or more of these species are also contemplated.

In an embodiment, soybean oil or another vegetable oil or glyceride ester may be modified by substitution of an cyclic moiety or acyclic ketone for one, two, or three ethylenic double bonds per fatty acyl moiety, analogous to the illustrations in FIG. 3. For example, a linolenic acyl moiety of a soybean oil triglyceride (which in nature is unsaturated at the 9, 12, and 15 positions) can be modified by converting the ethylenic double bond at the 15 position to a dihydrofuran, as shown in FIG. 3. Either that mono-substituted linolenic acyl or linoleic acyl, either of which in nature has ethylenic unsaturation at the 9 and 12 positions, can be reacted as shown in FIG. 3 by converting the ethylenic double bond at the 12 position to an dihydrofuran moiety. Either that di-ketone-substituted linolenic acyl, that monosubstituted linoleic acyl, or oleic acyl, any of which has ethylenic unsaturation at the 9 position (in nature), can be reacted as shown in FIG. 3 by converting the ethylenic double bond at the 9 position to a dihydrofuran, leaving a saturated acyl moiety with one, two, or three ketone moieties, respectively.

The preceding paragraph identifies naturally occurring positions of double bonds in soybean triglycerides. Processing techniques are known that can shift the double bonds from their positions in nature. For example, conjugation reactions can be used to shift the double bond positions. For another example, the bond positions can shift to a greater or lesser extent during partial hydrogenation depending upon the choice of catalyst and the conditions employed. Unless otherwise stated, therefore, the present stabilization of fatty acids and glycerides can be carried out using fatty acids and glycerides having either the bond positions found in nature or modified positions resulting either deliberately or as a by-product of processing.

The substitution of the dihydrofuran structure can be carried out, for example, as shown in FIG. 3, in which an olefin is reacted with a ketone in the presence of $Mn^{+3}$ as an electron acceptor to form the illustrated substituted 2,3-dihydrofuran ring, one ring member of which is a carbonyl moiety, in place of the site of unsaturation of the olefin starting material.

An unsaturated free fatty acid or acyl moiety has been modified to reduce the amount of unsaturation by reacting an ethylenic double bond to produce a dihydrofuran structure on the fatty acid chain. Such dihydrofuran structures on fatty acid chains are contemplated to be produced using both a fatty acid mixture that is mainly oleic acid and soybean oil as starting materials. Analysis of the reacted fatty acid mixture or with the reacted soybean oil shows that the fatty acid composition as determined by gas chromatography (GC) analysis of methyl esters has changed compared to the starting material. It is contemplated that this change includes reformation of an ethylenic double bond as a linked-in dihydrofuran moiety in the hydrocarbon chain of the acyl moiety.

It is also contemplated to modify any unsaturated free fatty acid by conversion of some or all of its ethylenic double bonds to dihydrofuran moieties, and then make esters with the dihydrofuran modified fatty acids to gain the benefits of this approach to stabilizing triglycerides or esters to oxidation.

It is also contemplated to modify any unsaturated fatty acyl moiety of a triglyceride by conversion of some or all of its ethylenic double bonds to dihydrofuran moieties, and then trans-esterify the fatty acids to gain the benefits of this approach to stabilizing triglycerides or esters to reduce oxidation.

It is further contemplated to prepare a dihydrofuran analog of any lubricant species containing ethylenic unsaturation, either by reacting the lubricant species directly or by reacting a precursor having ethylenic unsaturation as described here with a ketone as described here in the presence of a metal ion or other electron acceptor.

In certain embodiments, a vinyl structure is contemplated in which a vinyl moiety is substituted for at least one, alternatively two, alternatively three, alternatively four, alternatively five, alternatively six, alternatively all, of the ethylenic double bonds on at least one fatty acid chain of an unsaturated fatty acyl moiety of a free fatty acid, glyceride or other ester.

Alternatively, an embodiment is contemplated which is the partial or complete vinyl analog of an olefin. In this embodiment, the olefin is alternatively palmitoleic acid, oleic acid, linoleic acid, linolenic acid, alpha-eleostearic acid, ricinoleic acid, gadoleic acid, arachidonic acid, cetoleic acid, erucic acid, or any of the unsaturated acids shown in KIRK-OTHMER, ENCYCLOPEDIA OF SCIENCE AND TECHNOLOGY, $4^{th}$ Ed., Vol. 10, page 254 or any combination of two or more of these. A vinyl moiety can be substituted for one, alternatively two, alternatively three, alternatively four, alternatively five, alternatively six, alternatively all, of the ethylenic double bonds on at least one fatty acid chain of an unsaturated fatty acyl moiety of a free fatty acid, glyceride or other ester. The free fatty acid, glyceride, or other ester can be any material known for use as a lubricant, alone or in combination with other ingredients.

Alternatively soybean oil or another vegetable oil may be modified by substitution of a vinyl moiety for one, two, or three ethylenic double bonds per fatty acyl moiety. For example, a linolenic acyl moiety of a soybean oil triglyceride (which is unsaturated at the 9, 12, and 15 positions) is modified by converting the ethylenic double bond at the 15 position to a pendant vinyl moiety. Either that mono-substituted linolenic acyl or linoleic acyl, either of which has ethylenic unsaturation at the 9 and 12 positions, can be reacted by converting the ethylenic double bond at the 12 position to a pendant vinyl moiety. Either that di-substituted linolenic acyl, that monosubstituted linoleic acyl, or oleic acyl, any of which has ethylenic unsaturation at the 9 position, can be reacted by converting the ethylenic double bond at the 9 position to a pendant vinyl moiety, leaving a saturated acyl moiety with one, two, or three vinyl moieties, respectively.

The starting triglyceride oils have the formula:

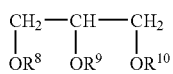

In this formula, $R^8$, $R^9$, and $R^{10}$ are independently any fatty acyl moiety corresponding to one of the fatty acids listed in the Kirk-Othmer table incorporated by reference, with the restriction that at least one of $R^8$, $R^9$, and $R^{10}$ is an ethylenically unsaturated acyl moiety available for lactone substitution. The carbonyl moieties of $R^8$, $R^9$, and $R^{10}$ are linked to the respective oxygen atoms of the nucleus shown above to form ester linkages. Each triglyceride has three fatty acyl groups, so a large number of different triglyceride species are present in a natural triglyceride oil.

Alternatively, $R^8$, $R^9$, and $R^{10}$ are predominantly acyls of any of the most abundant fatty acids, which are stearic acid, palmitic acid, oleic acid, linoleic acid, linolenic acid, and palmitoleic acid. Of these, stearic acid and palmitic acid have no ethylenic double bonds, and the others have one ethylenic double bond (oleic and palmitoleic acids), two ethylenic double bonds (linoleic acid), or three ethylenic double bonds (linolenic acid). The combinations of $R^8$, $R^9$, and $R^{10}$ on the most abundant species of triglycerides in soybean oil are provided in Table 1 of triglyceride acyls.

TABLE 1

Triglyceride Acyls

| Glyceride Species | $R^8$ | $R^9$ | $R^{10}$ |
|---|---|---|---|
| 1. | stearic acyl | stearic acyl | palmitoleic acyl |
| 2. | stearic acyl | stearic acyl | oleic acyl |
| 3. | stearic acyl | stearic acyl | linoleic acyl |
| 4. | stearic acyl | stearic acyl | linolenic acyl |
| 5. | stearic acyl | palmitoleic acyl | palmitoleic acyl |
| 6. | stearic acyl | palmitoleic acyl | oleic acyl |
| 7. | stearic acyl | palmitoleic acyl | linoleic acyl |
| 8. | stearic acyl | palmitoleic acyl | linolenic acyl |
| 9. | stearic acyl | oleic acyl | oleic acyl |
| 10. | stearic acyl | oleic acyl | linoleic acyl |
| 11. | stearic acyl | oleic acyl | linolenic acyl |
| 12. | stearic acyl | linoleic acyl | linoleic acyl |
| 13. | stearic acyl | linoleic acyl | linolenic acyl |
| 14. | stearic acyl | linolenic acyl | linolenic acyl |
| 15. | palmitoleic acyl | palmitoleic acyl | palmitoleic acyl |
| 16. | palmitoleic acyl | palmitoleic acyl | oleic acyl |
| 17. | palmitoleic acyl | palmitoleic acyl | linoleic acyl |
| 18. | palmitoleic acyl | palmitoleic acyl | linolenic acyl |
| 19. | palmitoleic acyl | oleic acyl | oleic acyl |
| 20. | palmitoleic acyl | oleic acyl | linoleic acyl |
| 21. | palmitoleic acyl | oleic acyl | linolenic acyl |
| 22. | palmitoleic acyl | linoleic acyl | linolenic acyl |
| 23. | palmitoleic acyl | linolenic acyl | linolenic acyl |
| 24. | oleic acyl | oleic acyl | oleic acyl |
| 25. | oleic acyl | oleic acyl | linoleic acyl |
| 26. | oleic acyl | oleic acyl | linolenic acyl |
| 27. | oleic acyl | linoleic acyl | linoleic acyl |
| 28. | oleic acyl | linoleic acyl | linolenic acyl |
| 29. | oleic acyl | linolenic acyl | linolenic acyl |
| 30. | linoleic acyl | linoleic acyl | linoleic acyl |
| 31. | linoleic acyl | linoleic acyl | linolenic acyl |
| 32. | linoleic acyl | linolenic acyl | linolenic acyl |
| 33. | linolenic acyl | linolenic acyl | linolenic acyl |

The triglycerides are reacted as described in this specification to substitute a lactone, ketone, dihydrofuran, or vinyl moiety for one or more ethylenic double bonds. It is contemplated that, for a particular fatty acyl moiety having more than one site of unsaturation, the lactone, ketone, dihydrofuran and/or vinyl substitution can be partial or complete. It is contemplated that the first site that will be substituted is the highest-numbered site of unsaturation, and additional sites will be substituted in descending numerical order. It is further contemplated that, when a triglyceride having two or three different types of unsaturated acyl moieties is reacted to substitute lactone, ketone, dihydrofuran, or vinyl moieties for ethylenic double bonds, assuming enough of the substituent reactant and any necessary catalyst is present, identically numbered sites of unsaturation generally will be in the same state (either substituted or unsubstituted) after the reaction, although the invention is not limited to instances in which these assumptions are correct.

The oils contemplated for use in the reactions described herein include soybean oil, canola oil, high oleic canola oil, cottonseed oil, rapeseed oil, palm oil, palm oil fraction, corn oil triglycerides, triglycerides made from fatty acids and glycerol such as glycerol trioleate made from distilled tall oil, or a combination of two or more of these. Partially hydrogenated forms of any of the above oil triglycerides may also be used.

The acids contemplated for use in the lactone reaction include any carboxylic acid having two or more carbon atoms, for example, acetic, propanoic, butanoic, pentanoic, and hexanoic acid. It has been further observed that the reaction rate may be increased by providing, in addition, a trace amount (e.g., 2 to 3 drops in a 100 ml reaction vessel) of acetone.

The ketones contemplated for use in the ketone reactions of FIG. 2 include any ketone having three or more carbon atoms, for example, acetone, pentane-2,4-dione, hexane-2,5-dione, diacetyl, benzophenone, cyclohexanone, diacetone alcohol, diisobutyl ketone, isophorone, methyl amyl ketone, methyl ethyl ketone, methyl isoamyl ketone, and methyl isobutyl ketone. The monofunctional ketones specified above are contemplated to be useful for substituting acyclic pendant ketone moieties or fused dihydrofuran rings for sites of olefinic unsaturation. These are acetone, benzophenone, cyclohexanone, diacetone alcohol (which has one ketone functional group and one hydroxyl functional group), diisobutyl ketone, isophorone, methyl amyl ketone, methyl ethyl ketone, methyl isoamyl ketone, and methyl isobutyl ketone. Examples of the difunctional ketones specified above are pentane-2,4-dione, hexane-2,5-dione, and diacetyl.

The metal cations contemplated for use in the lactone reaction include an ion of manganese (Mn), vanadium (V), cerium (Ce), with any suitable anion or combination of anions. One contemplated anion is a deprotonated carboxylic acid (i.e. carboxyl) moiety. While metal ions are preferred for certain embodiments, the reactions contemplated may be carried out in the presence of any suitable electron acceptor. Alternatively, the use of, for example, an $Mn^{+3}$ salt, such as manganese (III) acetylacetonate:

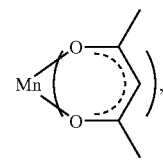

as the source of the metal, e.g., $Mn^{+3}$, ion may have the advantage of greater solubility in the reaction mixtures, thus allowing the use of a more favorable charge ratio than when forming, e.g., $Mn^{+3}$ acetate in situ. In other words, for a vessel of a given volume, the need for far less solvent for the catalyst component leaves correspondingly more vessel volume available for the vegetable oil reactant and the desired modified vegetable oil reaction product. Using such a source of the $Mn^{+3}$ ion may speed the reaction compared to a reaction run by generating the $Mn^{+3}$ salt in situ. Additionally, used at catalytic level, the $Mn^{+3}$ salt, e.g., manganese (III) acetylacetonate, may speed the lactone-forming reaction.

The most common reaction products of the various substitution reactions (lactone, ketone, dihydrofuran, and/or vinyl) carried out on a homogeneous triglyceride (i.e. $R^8$, $R^9$, and $R^{10}$ are the same fatty acyl moiety) or heterogeneous triglyceride (i.e. $R^8$, $R^9$, and $R^{10}$ are two or three different fatty acyl moieties) are summarized in the Table 2 of Reaction Products, in which each combination of $R^8$, $R^9$, and $R^{10}$ according to the above triglyceride structure is presented as one of the rows in the table.

TABLE 2

| Reaction Products | | | |
|---|---|---|---|
| Glyceride Species | $R^{11}$ | $R^{12}$ | $R^{13}$ |
| 34. | stearic acyl | stearic acyl | palmitoleic acyl with a substitution at the 9 position |
| 35. | stearic acyl | stearic acyl | oleic acyl with a substitution at the 9 position |
| 36. | stearic acyl | stearic acyl | linoleic acyl with a substitution at the 12 position |
| 37. | stearic acyl | stearic acyl | linoleic acyl with substitutions at the 9 and 12 positions |
| 38. | stearic acyl | stearic acyl | linolenic acyl with a substitution at the 15 position |
| 39. | stearic acyl | stearic acyl | linolenic acyl with substitutions at the 12 and 15 positions |
| 40. | stearic acyl | stearic acyl | linolenic acyl with substitutions at the 9, 12 and 15 positions |
| 41. | stearic acyl | palmitoleic acyl with a substitution at the 9 position | palmitoleic acyl with a substitution at the 9 position |
| 42. | stearic acyl | palmitoleic acyl with a substitution at the 9 position | oleic acyl with a substitution at the 9 position |
| 43. | stearic acyl | palmitoleic acyl | linoleic acyl with a substitution at the 12 position |
| 44. | stearic acyl | palmitoleic acyl with a substitution at the 9 position | linoleic acyl with substitutions at the 9 and 12 positions |
| 45. | stearic acyl | palmitoleic acyl | linolenic acyl with a substitution at the 15 position |
| 46. | stearic acyl | palmitoleic acyl | linolenic acyl with substitutions at the 12 and 15 positions |
| 47. | stearic acyl | palmitoleic acyl with a substitution at the 9 position | linolenic acyl with substitutions at the 9, 12 and 15 positions |
| 48. | stearic acyl | oleic acyl with a substitution at the 9 position | oleic acyl with a substitution at the 9 position |
| 49. | stearic acyl | oleic acyl | linoleic acyl with a substitution at the 12 position |
| 50. | stearic acyl | oleic acyl with a substitution at the 9 position | linoleic acyl with substitutions at the 9 and 12 positions |
| 51. | stearic acyl | oleic acyl | linolenic acyl with a substitution at the 15 position |
| 52. | stearic acyl | oleic acyl | linolenic acyl with I substitutions at the 12 and 15 positions |
| 53. | stearic acyl | oleic acyl with a substitution at the 9 position | linolenic acyl with substitutions at the 9, 12 and 15 positions |
| 54. | stearic acyl | linoleic acyl with a substitution at the 12 position | linoleic acyl with a substitutions at the 12 position |
| 55. | stearic acyl | linoleic acyl with substitutions at the 9 and 12 positions | linoleic acyl with substitutions at the 9 and 12 positions |
| 56. | stearic acyl | linoleic acyl | linolenic acyl with a substitution at the 15 position |
| 57. | stearic acyl | linoleic acyl with a substitution at the 12 position | linolenic acyl with substitutions at the 12 and 15 positions |
| 58. | stearic acyl | linoleic acyl with substitutions at the 9 and 12 positions | linolenic acyl with substitutions at the 9, 12 and 15 positions |
| 59. | stearic acyl | linolenic acyl with a substitution at the 15 position | linolenic acyl with a substitution at the 15 position |
| 60. | stearic acyl | linolenic acyl with substitutions at the 12 and 15 positions | linolenic acyl with substitutions at the 12 and 15 positions |
| 61. | stearic acyl | linolenic acyl with substitutions at the 9, 12 and 15 positions | linolenic acyl with substitutions at the 9, 12 and 15 positions |
| 62. | palmitoleic acyl | palmitoleic acyl with a substitution at the 9 position | palmitoleic acyl with a substitution at the 9 position |
| 63. | palmitoleic acyl with a substitution at the 9 position | palmitoleic acyl with a substitution at the 9 position | oleic acyl with a substitution at the 9 position |
| 64. | palmitoleic acyl | palmitoleic acyl | linoleic acyl with a substitution at the 12 position |
| 65. | palmitoleic acyl with a substitution at the 9 position | palmitoleic acyl with a substitution at the 9 position | linoleic acyl with substitutions at the 9 and 12 positions |
| 66. | palmitoleic acyl | palmitoleic acyl | linolenic acyl with a substitution at the 15 position |
| 67. | palmitoleic acyl | palmitoleic acyl | linolenic acyl with substitutions at the 12 and 15 positions |
| 68. | palmitoleic acyl with a substitution at the 9 position | palmitoleic acyl with a substitution at the 9 position | linolenic acyl with substitutions at the 9, 12 and 15 positions |

TABLE 2-continued

Reaction Products

| Glyceride Species | R[11] | R[12] | R[13] |
|---|---|---|---|
| 69. | palmitoleic acyl with a substitution at the 9 position | oleic acyl with a substitution at the 9 position | oleic acyl with a substitutions at the 9 position |
| 70. | palmitoleic acyl | oleic acyl | linoleic acyl with a substitution at the 12 position |
| 71. | palmitoleic acyl with a substitution at the 9 position | oleic acyl with a substitution at the 9 position | linoleic acyl with substitutions at the 9 and 12 positions |
| 72. | palmitoleic acyl | oleic acyl | linolenic acyl with a substitution at the 15 position |
| 73. | palmitoleic acyl | oleic acyl | linolenic acyl with substitutions at the 12 and 15 positions |
| 74. | palmitoleic acyl with a substitution at the 9 position | oleic acyl with a substitution at the 9 position | linolenic acyl with substitutions at the 9, 12 and 15 positions |
| 75. | palmitoleic acyl | linoleic acyl | linolenic acyl with a substitution at the 15 position |
| 76. | palmitoleic acyl | linoleic acyl with a substitution at the 12 position | linolenic acyl with substitutions at the 12 and 15 positions |
| 77. | palmitoleic acyl with a substitution at the 9 position | linoleic acyl with substitutions at the 9 and 12 positions | linolenic acyl with substitutions at the 9, 12 and 15 positions |
| 78. | palmitoleic acyl | linolenic acyl with a substitution at the 15 position | linolenic acyl with a substitution at the 15 position |
| 79. | palmitoleic acyl | linolenic acyl with substitutions at the 12 and 15 positions | linolenic acyl with substitutions at the 12 and 15 positions |
| 80. | palmitoleic acyl with a substitution at the 9 position | linolenic acyl with substitutions at the 9, 12 and 15 positions | linolenic acyl with substitutions at the 9, 12 and 15 positions |
| 81. | oleic acyl with a substitution at the 9 position | oleic acyl with a substitution at the 9 position | oleic acyl with a substitution at the 9 position |
| 82. | oleic acyl | oleic acyl | linoleic acyl with a substitution at the 12 position |
| 83. | oleic acyl with a substitution at the 9 position | oleic acyl with a substitution at the 9 position | linoleic acyl with substitutions at the 9 and 12 positions |
| 84. | oleic acyl | oleic acyl | linolenic acyl with a substitution at the 15 position |
| 85. | oleic acyl | oleic acyl | linolenic acyl with substitutions at the 12 and 15 positions |
| 86. | oleic acyl with a substitution at the 9 position | oleic acyl with a substitution at the 9 position | linolenic acyl with substitutions at the 9, 12 and 15 positions |
| 87. | oleic acyl | linoleic acyl with a substitution at the 12 position | linoleic acyl with a substitution at the 12 position |
| 88. | oleic acyl with a substitution at the 9 position | linoleic acyl with substitutions at the 9 and 12 positions | linoleic acyl with substitutions at the 9 and 12 positions |
| 89. | oleic acyl | linoleic acyl | linolenic acyl with a substitution at the 15 position |
| 90. | oleic acyl | linoleic acyl with a substitution at the 12 position | linolenic acyl with substitutions at the 12 and 15 positions |
| 91. | oleic acyl with a substitution at the 9 position | linoleic acyl with substitutions at the 9 and 12 positions | linolenic acyl with substitutions at the 9, 12 and 15 positions |
| 92. | oleic acyl | linolenic acyl with a substitution at the 15 position | linolenic acyl with a substitution at the 15 position |
| 93. | oleic acyl | linolenic acyl with substitutions at the 12 and 15 positions | linolenic acyl with substitutions at the 12 and 15 positions |
| 94. | oleic acyl with a substitution at the 9 position | linolenic acyl with substitutions at the 9, 12 and 15 positions | linolenic acyl with substitutions at the 9, 12 and 15 positions |
| 95. | linoleic acyl with a substitution at the 12 position | linoleic acyl with a substitution at the 12 position | linoleic acyl with a substitution at the 12 position |
| 96. | linoleic acyl with substitutions at the 9 and 12 positions | linoleic acyl with substitutions at the 9 and 12 positions | linoleic acyl with substitutions at the 9 and 12 positions |
| 97. | linoleic acyl | linoleic acyl | linolenic acyl with a substitution at the 15 position |
| 98. | linoleic acyl with a substitution at the 12 position | linoleic acyl with a substitution at the 12 position | linolenic acyl with substitutions at the 12 and 15 positions |
| 99. | linoleic acyl with substitutions at the 9 and 12 positions | linoleic acyl with substitutions at the 9 and 12 positions | linolenic acyl with substitutions at the 9, 12 and 15 positions |
| 100. | linoleic acyl | linolenic acyl with a substitution at the 15 position | linolenic acyl with a substitution at the 15 position |
| 101. | linoleic acyl with a substitution at the 12 position | linolenic acyl with substitutions at the 12 and 15 positions | linolenic acyl with substitutions at the 12 and 15 positions |
| 102. | linoleic acyl with substitutions at the 9 and 12 positions | linolenic acyl with substitutions at the 9, 12 and 15 positions | linolenic acyl with substitutions at the 9, 12 and 15 positions |
| 103. | linolenic acyl with a substitution at the 15 position | linolenic acyl with a substitution at the 15 position | linolenic acyl with a substitution at the 15 position |
| 104. | linolenic acyl with substitutions at the 12 and 15 positions | linolenic acyl with substitutions at the 12 and 15 positions | linolenic acyl with substitutions at the 12 and 15 positions |
| 105. | linolenic acyl with substitutions at the 9, 12 and 15 positions | linolenic acyl with substitutions at the 9, 12 and 15 positions | linolenic acyl with substitutions at the 9, 12 and 15 positions |

It is contemplated that in certain embodiments, the substituted structures are more stable to oxidation than the double bond for which they are substituted. In certain embodiments, the lactone or dihydrofuran ring structure, the ketone pendant group, or the pendant vinyl group inhibit crystallization of the oil. Differential scanning calorimetry (DSC) data, discussed more fully in the examples below, indicates that with increasing level of treatment the lactone and ketone reaction products show reduced crystallinity. Measuring the area under the DSC curve is useful for determining the extent of crystallinity. The invention is not, however, limited to embodiments having these properties.

This development is contemplated to allow one or both of the two principal shortcomings of vegetable oils in terms of many industrial uses, relatively low oxidative stability and relatively high pour points, to be addressed with a single reaction chemistry that is easy to carry out and uses relatively low cost reactants. The degree of modification of the starting material can be tailored to match the end use of the product.

In one alternative, vegetable oil modified as described can comprise the lubricant or one of the lubricant components of a lubricant added to gasoline for lubricating two-cycle gasoline engines. A gasoline-based fuel containing one or more vegetable oils modified as described is also contemplated.

In another alternative, vegetable oil modified as described can comprise the lubricant or one of the lubricant components of a textile fiber lubricant.

In another alternative, vegetable oils modified as described can comprise the lubricant or one of the lubricant components of a metalworking, metal forming, metal cutting, die casting, or other metal processing oil or fluid.

For example, a suitable metalworking, metal forming, metal cutting, die casting, or other metal processing oil or fluid can be a triglyceride, such as a vegetable oil, modified as described in any embodiment above and either used neat or dispersed in an aqueous or non-aqueous carrier phase.

In another alternative, vegetable oils modified as described comprise the mold release agent or a component of a mold release agent for plastics and rubber. For example, a suitable mold release agent can be a triglyceride, such as a vegetable oil, modified as described in any embodiment above and either used neat or dispersed in an aqueous or non-aqueous carrier phase.

One method of characterizing oxidative stability is known as thin film micro-oxidation (TFMO). An example of this method is provided in W. Castro, J. M. Erhan, S. Z. Erhan and F. Caputo, *A Study of the Oxidation and Wear Properties of Vegetable Oils: Soybean Oil without Additives*, J. AMER. OIL. CHEM. SOC., 83(1) 2006 p. 47-52, which is incorporated by reference in its entirety.

To characterize the oxidative stability of the reaction products described herein, the above method has been modified somewhat. Briefly, the subject oil is applied by micropipette to a weighing pan for a microbalance to create a thin film and weighed. The weighed pan is placed in clean glass reaction tubes. The tubes are placed in a heating block with an air flow of approximately 20 ml/min being maintained over the oil sample. The oil sample is heated for a given time, such a 30 minutes, 60 minutes, 90 minutes or 120 minutes, and given temperature, such as 150° C., 175° C. or 200° C. The pans containing the oil samples are allowed to cool and then weighed. The difference between the original sample weight and the sample weight after heating is the evaporation loss, which can be expressed as a percentage called percent volatiles. The pans containing the oxidized samples are then washed in an organic solvent such as tetrahydrofuran (THF) to remove soluble oil. Other solvents could be used. The pans, with depositing remaining on them after the washing step, are placed in a dessicator to dry. Once dry, the pans are again weighed. From the difference between the original sample weight and the sample weight after washing, one can determine the weight of the deposits left in the pan, which can be expressed as a percentage called percent deposits.

The free radical chemistry is contemplated to react more strongly with polyunsaturated fatty acids than with monounsaturated fatty acids so the modification tends to target the formation of reaction products in a way to get the greatest benefit for any given level of treatment.

The present reaction products are contemplated to be useful and to achieve a technical effect as lubricants, or as ingredients of a lubricant formulation. Alternatively, the present reaction products are contemplated to be useful and to achieve a technical effect as hydraulic fluids, or as ingredients of a hydraulic fluid formulation. Alternatively, the present reaction products are contemplated to be useful and to achieve a technical effect as dielectric fluids, including dielectric cooling fluids, or as ingredients of a dielectric fluid formulation.

It is further contemplated that after running the lactone, ketone, or vinyl reactions, the resulting products could be hydrogenated to remove residual double bonds in the fatty acid chains. Hydrogenation of the ketone reaction products is contemplated to lead to useful polyol intermediates for other reaction chemistries. Alternatively, hydrogenation of the reaction products of certain embodiments of the vinyl grafting chemistry is contemplated to lead to a highly stable final product if no additional oxygen atoms are added to the final reaction products in the form of a carbonyl, ester, or hydroxyl group.

It is further contemplated that the ketone structure of certain embodiments provides a way for further modification of the ketone chemistry reaction products by incorporating a hydroxyl group. Hydroxyl groups may be provided in certain embodiments by running the reaction in the presence of water. A hydroxyl group provides a novel path to polyol production from vegetable oils. Vegetable based polyols are contemplated to be useful in the manufacture of biologically-based polyurethane polymers. Further, reacting the hydroxyl group via an ester linkage may be used to form further appendages. Vegetable based polyols produced in accordance with certain embodiments of the ketone chemistry may behave as emulsifiers depending upon the average number of hydroxyl groups per triglyceride molecule.

The following examples are provided to illustrate the invention and how to practice it. The scope of the invention is not limited by these examples or the remainder of the specification, but is defined solely by the claims.

Example 1

Preparation of $Mn^{+3}$ 78.1 g. $Mn_2O_3$ is placed in a 1-liter reactor, which is then rinsed down with 28.3 g. glacial acetic acid. 151.5 g. acetic anhydride are added, forming a black slurry. An additional 236.8 g. glacial acetic acid is added, and the mixture is allowed to stand for about four hours at room temperature. The reaction mixture is then heated using an electric heater, gradually raising its temperature to 104° C. after about three hours. The temperature remains at 104° C. for an additional 45 minutes, after which the heat is turned off and the mixture is allowed to cool overnight. The product is contemplated to contain:

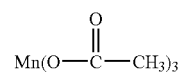

$(Mn(OAc)_3)$ in acetic anhydride, which is referred to in this specification as an $Mn^{+3}$ mixture. In the above formula, three deprotonated carboxylic acid moieties are anions associated with the Mn cation.

Example 2

Conversion of Olefin to Lactone 20.0 g. of acetic acid are added to 100.0 g. of soybean oil. 16.1 g. of the $Mn^{+3}$ mixture produced in Example 1 is added. The reaction mixture is heated to 50° C., then allowed to cool to ambient room temperature for 12 hours. The product is contemplated to contain triglycerides in which lactone moieties are formed at the sites of at least some of the olefinic double bonds. A sample is taken, then this product is heated in a glass double boiler to 70° C.-80° C. and held for one hour at that temperature. The product is then allowed to cool to room temperature. The product is contemplated to contain triglycerides in which lactone moieties are formed at the sites of at least some of the olefinic double bonds.

Example 3

Conversion of Olefin to Lactone 16.0 g. of the $Mn^{+3}$ mixture produced in Example 1 is heated to 50° C., then added to 100 g. of soybean oil held at room temperature and reacted, then heated in a double boiler and held for one hour at 75 to 95° C. The product is contemplated to contain triglycerides in which lactone moieties are formed at the sites of at least some of the olefinic double bonds.

Example 4

Different Lactone Species

The reaction of each preceding example is repeated multiple times, using as the olefin in different trials: 1-dodecene, 90% oleic acid, low saturated soy acids, soy oil, and 1 g. of each of the preceding olefins combined with 1 g. of water. The successful reaction products are shown by gas chromatography to be different from the reactants. The products are contemplated to be the lactones indicated in FIG. 1.

Example 5

Soybean Oil with Lactone Modification 27.0 g. $Mn(OAc)_2 \cdot 4H_2O$ and 139.5 g. of acetic acid are mixed in a reaction vessel. 4.1 g. of $KMnO_4$ is added. 48.1 g. acetic anhydride is added. 25.1 g. of a refined, bleached and deodorized soybean oil (sold under the trademark IMPERIAL VEGETABLE OIL®) is added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 1757.

Example 6

Soybean Oil with Ketone Modification 27.0 g. $Mn(OAc)_2 \cdot 4H_2O$ and 139.9 g. of acetic acid are mixed in a reaction vessel. 4.1 g. of $KMnO_4$ is added. 48.4 g. acetic anhydride is added. 25.1 g. of a refined, bleached and deodorized soybean oil and 200 ml of acetone are added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 2, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 1756.

TABLE 3

Substituents of Working Example Products

| Ex. | R5 | R6 | R7 |
|---|---|---|---|
| 5 | H | H | — |
| 6 | methyl | methyl | — |
| 7 | H | H | — |
| 8 | methyl | methyl | — |
| 9 | H | H | — |
| 10 | methyl | methyl | — |
| 11 | H | H | — |
| 12 | methyl | methyl | — |
| 13 | H | H | — |
| 14 | methyl | methyl | — |
| 15 | H | H | — |
| 16 | methyl | methyl | — |
| 23 | H | H | — |
| 24 | H | H | — |
| 25 | H | H | — |
| 26 | H | H | — |
| 27 | H | H | — |
| 28 | H | H | — |
| 29 | H | H | — |
| 30 | H | H | — |
| 31 | H | H | — |
| 32 | H | H | — |
| 33 | — | methyl | Methyl-carbonyl |

Example 7

Soybean Oil with Lactone Modification 27.0 g. $Mn(OAc)_2 \cdot 4H_2O$ and 139.7 g. of acetic acid are mixed in a reaction vessel. 4.1 g. of $KMnO_4$ is added. 49.2 g. acetic anhydride is added. 7.6 g. of a refined, bleached and deodorized soybean oil is added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 0458.

Example 8

Soybean Oil with Ketone Modification 27.0 g. $Mn(OAc)_2 \cdot 4H_2O$ and 139.5 g. of acetic acid are mixed in a reaction vessel. 4.1 g. of $KMnO_4$ is added. 47.7 g. acetic anhydride is added. 7.5 g. of a refined, bleached and deodorized soybean oil and 200 ml of acetone are added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 2, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 0459.

Example 9

Partially Hydrogenated Soybean Oil with Lactone Modification 27.0 g. $Mn(OAc)_2.4H_2O$ and 139.5 g. of acetic acid are mixed in a reaction vessel. 4.1 g. of $KMnO_4$ is added. 47.8 g. acetic anhydride is added. 12.0 g. of a refined, bleached and partially hydrogenated soybean oil is added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 1085.

Example 10

Partially Hydrogenated Soybean Oil with Ketone Modification 27.0 g. $Mn(OAc)_2.4H_2O$ and 139.5 g. of acetic acid are mixed in a reaction vessel. 4.1 g. of $KMnO_4$ is added. 47.9 g. acetic anhydride is added. 12.0 g. of a refined, bleached and partially hydrogenated soybean oil and 200 ml of acetone are added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 2, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 1086.

Example 11

Partially Hydrogenated Soybean Oil with Lactone Modification 27.0 g. $Mn(OAc)_2.4H_2O$ and 139.6 g. of acetic acid are mixed in a reaction vessel. 4.1 g. of $KMnO_4$ is added. 47.6 g. acetic anhydride is added. 23.6 g. of a refined, bleached and partially hydrogenated soybean oil is added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 0823.

Example 12

Partially Hydrogenated Soybean Oil with Ketone Modification 27.0 g. $Mn(OAc)_2.4H_2O$ and 139.5 g. of acetic acid are mixed in a reaction vessel. 4.1 g. of $KMnO_4$ is added. 48.0 g. acetic anhydride is added. 23.6 g. of a refined, bleached and partially hydrogenated soybean oil and 200 ml of acetone are added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 2, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 0824.

Example 13

High Oleic Canola Oil with Lactone Modification 27.0 g. $Mn(OAc)_2.4H_2O$ and 139.5 g. of acetic acid are mixed in a reaction vessel. 4.1 g. of $KMnO_4$ is added. 47.7 g. acetic anhydride is added. 8.8 g. of a refined, bleached and deodorized high oleic canola oil (sold under the trademark NUTRA-CLEAR NT®) is added to the vessel, along with a small drop of acetone. The vessel is heated and allowed to cool following reaction. The reaction undergoes a series of color changes over time. A precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 1346. This synthesis demonstrated the reaction's sensitivity to the presence of acetone, which accelerates the lactone modification.

Example 14

High Oleic Canola Oil with Ketone Modification 27.0 g. $Mn(OAc)_2.4H_2O$ and 140 g. of acetic acid are mixed in a reaction vessel. 4.1 g. of $KMnO_4$ is added. 47.6 g. acetic anhydride is added. 8.8 g. of a refined, bleached and and deodorized high oleic canola oil and 200 ml of acetone are added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 2, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 1347.

Example 15

Soybean Oil with Lactone Modification 27.0 g. $Mn(OAc)_2.4H_2O$ and 139.5 g. of acetic acid are mixed in a reaction vessel. 4.1 g. of $KMnO_4$ is added. 47.7 g. acetic anhydride is added. 25.4 g. of a soybean oil is added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. The reaction product is referred to in this specification as 1977.

Example 16

Soybean Oil with Ketone Modification 27.0 g. Mn(OAc)$_2$.4H$_2$O and 139.5 g. of acetic acid are mixed in a reaction vessel. 4.1 g. of KMnO$_4$ is added. 47.8 g. acetic anhydride is added. 25.4 g. of a soybean oil and 200 ml of acetone are added to the vessel, which is heated and allowed to cool following reaction. The reaction undergoes a series of color changes over time. A precipitate collects at the bottom of the vessel, which is contemplated to contain the triglyceride product having at least one oleic acyl moiety of FIG. 2, in which the R$^1$, R$^2$, R$^3$, and R$^4$ groups are at least essentially those of the reactant oil and the R$^5$, R$^6$, and R$^7$ groups are assigned as shown in Table 3. The reaction product is referred to in this specification as 1976.

Example 17

TFMO Characterization of Modified Soybean Oils

The following samples were characterized using the TFMO methodology described above: 1756 (the ketone carboxylate of Example 6), 1757 (the lactone of Example 5), 1976 (the ketone carboxylate of Example 16), 1977 (the lactone of Example 15), 0458 (the lactone of Example 7) and 0459 (the ketone carboxylate of Example 8). The samples were heated at 150° C. for 60 minutes and/or 120 minutes. The results are presented in Table 4.

TABLE 4

TFMO Characterization of Modified Soybean Oils at 150 C.

| SAMPLE | % Volatiles (60 minutes) | % Volatiles (120 minutes) | % Deposits (60 minutes) | % Deposits (120 minutes) |
| --- | --- | --- | --- | --- |
| 1757 | 4 | 7 | 8 | 34 |
| 1756 | 4 | 6 | 20 | 43 |
| 1976 |   | 3 |   | 25 |
| 1977 |   | 3 |   | 19 |
| 0458 |   | 1 |   | 1 |
| 0459 |   | 0 |   | 1 |
| Untreated oil |   | 2 |   | 17 |

Samples 0458 (the lactone of Example 7) and 0459 (the ketone carboxylate of Example 8) were also characterized using TFMO at 200° C. for 120 minutes. The results are presented in Table 5:

TABLE 5

TFMO Characterization of Modified Soybean Oils at 200 C.

| SAMPLE | % Volatiles (120 minutes) | % Deposits (120 minutes) |
| --- | --- | --- |
| 0458 | 5 | 8 |
| 0459 | 5 | 21 |

This example demonstrates that increasing the reactant concentrations, as in samples 0458 (the lactone of Example 7) and 0459, results in reaction products having an increased oxidative stability as compared to untreated oil and as compared to the reaction products of the lower concentration reactions.

Example 18

TFMO Characterization of Modified Partially Hydrogenated Soybean Oils

Samples 1085 (the lactone of Example 9) and 1086 (the ketone carboxylate of Example 10) (the ketone carboxylate of Example 10) were characterized using the TFMO methodology described above by heating at 200° C. for 60 minutes and 120 minutes. The results are presented in Table 6. Both samples appear to be oxidatively stable.

TABLE 6

TFMO Characterization of Modified Partially Hydrogenated Soybean Oils at 200 C.

| SAMPLE | % Volatiles (60 minutes) | % Volatiles (120 minutes) | % Deposits (60 minutes) | % Deposits (120 minutes) |
| --- | --- | --- | --- | --- |
| 1085 | 10 | 12 | 9 | 8 |
| 1086 | 8 | 11 | 7 | 17 |

Example 19

TFMO Characterization of Modified High Oleic Canola Oils

Samples 1346 (the lactone of Example 13) and 1347 (the ketone carboxylate of Example 14) were characterized using the TFMO methodology described above by heating at 200° C. for 60 minutes and 120 minutes. The results are presented in Table 7.

TABLE 7

TFMO Characterization of Modified High Oleic Canola Oils at 200 C.

| SAMPLE | % Volatiles (60 minutes) | % Volatiles (120 minutes) | % Deposits (60 minutes) | % Deposits (120 minutes) |
| --- | --- | --- | --- | --- |
| 1346 | 11 | 11 | 34 | 58 |
| 1347 | 6 | 9 | 5 | 6 |
| Untreated oil | 11 | 10 | 30 | 59 |

Sample 1346 (the lactone of Example 13) (lactone reaction product) appears to be as stable as the control oil. Sample 1347 (the ketone carboxylate of Example 14) demonstrates an improved oxidative stability.

Example 20

DSC Characterization of Modified Soybean Oils

DSC was performed on samples 1976 (the ketone carboxylate of Example 16) and 1977 (the lactone of Example 15) to characterize the changes in crystallinity resulting from modification. The DSC protocol was as follows: 1) Hold samples for 5.0 minutes at 25.00° C.; 2) Cool samples from 25.00° C. to −70.00° C. at a cooling rate of 10.00° C. per minute; 3) Hold samples for 30.0 minutes at −70.00° C.; 4) Heat samples from −70.00° C. to 25.00° C. at a heating rate of 5.00° C. per minute. The resulting data is presented in Table 8:

TABLE 8

DSC Characterization of Modified Soybean Oils

| SAMPLE | AREA UNDER DSC CURVE DURING COOLING (mJ) | AREA UNDER DSC CURVE DURING HEATING (mJ) |
|---|---|---|
| 1976 | 72.041 | −54.558 |
| 1977 | 37.563 | −70.257 |
| Untreated oil | 386.726 | −115.271 |

The decrease in the area under the DSC curve for both treated samples demonstrates a decrease in crystallinity for the treated soybean oils. This decrease in crystallinity correlates with improved low temperature performance and a decreased pour point. Additionally, an increase in the viscosity of the treated oils as compared to the untreated oil, along with a decrease in the rate of solidification, was visually observed.

Example 21

DSC Characterization of Modified Partially Hydrogenated Soybean Oils

DSC was performed on samples 0823 (the lactone of Example 11) and 0824 (the ketone carboxylate of Example 12) to characterize the changes in crystallinity resulting from modification. The DSC protocol was as follows: 1) Hold samples for 10.0 minutes at 80.00° C.; 2) Cool samples from 80.00° C. to −60.00° C. at a cooling rate of 10.00° C. per minute; 3) Hold samples for 30.0 minutes at −60.00° C.; 4) Heat samples from −60.00° C. to 80.00° C. at a heating rate of 5.00° C. per minute. The resulting data is presented in Table 9:

TABLE 9

DSC Characterization of Modified Partially Hydrogenated Soybean Oils

| SAMPLE | AREA UNDER DSC CURVE DURING COOLING (mJ) | AREA UNDER DSC CURVE DURING HEATING (mJ) |
|---|---|---|
| 0823 | 640.573 | −482.113 |
| 0824 | 179.290 | −335.421 |
| Untreated oil | 674.484 | −761.004 |

The decrease in the area under the DSC curve for both treated samples demonstrates a decrease in crystallinity for the treated partially hydrogenated soybean oils, in particular the ketone modified partially hydrogenated soybean oil. Additionally, an increase in the viscosity of the treated oils as compared to the untreated oil, along with a decrease in the rate of solidification, was visually observed.

Example 22

DSC Characterization of Modified High Oleic Canola Oils

DSC was performed on samples 1346 (the lactone of Example 13) and 1977 (the ketone carboxylate of Example 14) to characterize the changes in crystallinity resulting from modification. The DSC protocol was as follows: 1) Hold samples for 10.0 minutes at 80.00° C.; 2) Cool samples from 80.00° C. to −60.00° C. at a cooling rate of 10.00° C. per minute; 3) Hold samples for 30.0 minutes at −60.00° C.; 4) Heat samples from −60.00° C. to 80.00° C. at a heating rate of 5.00° C. per minute. The resulting data is presented in Table 10:

TABLE 10

DSC Characterization of Modified High Oleic Canola Oils

| SAMPLE | AREA UNDER DSC CURVE DURING COOLING (mJ) | AREA UNDER DSC CURVE DURING HEATING (mJ) |
|---|---|---|
| 1346 | 0 | 0 |
| 1977 | 16.930 | 0 |
| Untreated oil | 375.677 | 0 |

The decrease in the area under the DSC curve for both treated samples demonstrates a decrease in crystallinity for the treated high oleic canola oils. Additionally, an increase in the viscosity of the treated oils as compared to the untreated oil, along with a decrease in the rate of solidification, was visually observed.

Example 23

Soybean Oil with Lactone Modification 27.0 g. $Mn(OAc)_2.4H_2O$ and 139.6 g. of acetic acid are mixed in a reaction vessel. 4.1 g. of $KMnO_4$ is added. 48.3 g. acetic anhydride is added. 7.7 g. of a soybean oil is added to the vessel, along with 3 drops of acetone. The vessel is heated and allowed to cool following reaction. The reaction undergoes a series of color changes over time. Approximately 15 ml of a pink precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. Approximately 180 ml of orange yellow liquid remains.

Example 24

High Oleic Canola Oil with Lactone Modification 27.0 g. $Mn(OAc)_2.4H_2O$ and 139.5 g. of acetic acid are mixed in a reaction vessel. 4.1 g. of $KMnO_4$ is added. 48.1 g. acetic anhydride is added. 8.8 g. of a refined, bleached and deodorized high oleic canola oil is added to the vessel, along with 2 drops of acetone. The vessel is heated and allowed to cool following reaction. The reaction undergoes a series of color changes over time. A precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. This synthesis demonstrated the reaction's sensitivity to the presence of acetone, which accelerates the lactone modification.

Example 25

High Oleic Canola Oil with Lactone Modification 27.0 g. $Mn(OAc)_2.4H_2O$ and 139.5 g. of acetic acid are mixed in a reaction vessel. 4.1 g. of $KMnO_4$ is added. 47.8 g. acetic anhydride is added. 8.8 g. of a refined, bleached and deodorized high oleic canola oil is added to the vessel, along with 2 drops of acetone. The vessel is heated and allowed to cool following reaction. As compared to example 23, order of the addition of $KMnO_4$ is changed such that it is suspended above the reaction, interacting with the reaction vapor and thus being more slowly added. The reaction undergoes a series of color changes over time. A precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. This synthesis demonstrated the reaction's sensitivity to the presence of acetone, which accelerates the lactone modification.

Example 26

High Oleic Canola Oil with Lactone Modification 9.0 g. $Mn(OAc)_2.4H_2O$ and 139.8 g. of acetic acid are mixed in a reaction vessel. 4.1 g. of $KMnO_4$ is added. 15.9 g. acetic anhydride is added. 8.8 g. of a refined, bleached and deodorized high oleic canola oil is added to the vessel, along with 2 drops of acetone. The vessel is heated and allowed to cool following reaction. The reaction undergoes a series of color changes over time. A precipitate collects at the bottom of the vessel, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3. This synthesis demonstrated the reaction's sensitivity to the presence of acetone, which accelerates the lactone modification.

Example 27

Methyl-Oleate with Lactone Modification 3 g. $Mn^{+3}$ acetyl acetonate and 10 g. of acetic acid are mixed in a test tube. 2.5 g. of methyl oleate is added. The tube is heated and allowed to cool following reaction. The reaction undergoes a series of color changes over time. A precipitate collects at the bottom of the vessel, which is contemplated to contain the modified methyl oleate product having at least one oleic acyl moiety of FIG. 1, in which the $R^1$, $R^2$, $R^3$, and $R^4$ groups are at least essentially those of the reactant oleate and the $R^5$, $R^6$, and $R^7$ groups are assigned as shown in Table 3. This example is repeated changing 3 g. $Mn^{+3}$ acetyl acetonate to 1.5 g.

Example 28

Soybean Oil with Lactone Modification 27.0 g. $Mn(OAc)_2.4H_2O$ and 139.7 g. of acetic acid are mixed in a reaction vessel. 4.1 g. of $KMnO_4$ is added. 49.7 g. acetic anhydride is added. 7.8 g. of a soybean oil is added to the vessel, along with 0.5 g. of $Mn^{+3}$ acetyl acetonate. The vessel is heated and allowed to cool following reaction. The reaction undergoes a series of color changes over time. A precipitate collects at the bottom of the tube, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3.

Example 29

Soybean Oil with Lactone Modification 3 g. $Mn^{+3}$ acetyl acetonate and 10 g. of acetic acid are mixed in a test tube. 2.0 g. of soybean oil is added. The tube is heated and allowed to cool following reaction. The reaction undergoes a series of color changes over time. A precipitate collects at the bottom of the tube, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3.

Example 30

High Oleic Canola Oil with Lactone Modification 3 g. $Mn^{+3}$ acetyl acetonate and 10 g. of acetic acid are mixed in a test tube. 2.0 g. of high oleic canola oil is added. The tube is heated and allowed to cool following reaction. The reaction undergoes a series of color changes over time. A precipitate collects at the bottom of the tube, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3.

Example 31

Hydrogenated Soybean Oil with Lactone Modification 3 g. $Mn^{+3}$ acetyl acetonate and 10 g. of acetic acid are mixed in a test tube. 2.0 g. of hydrogenated soybean oil is added. The tube is heated and allowed to cool following reaction. The reaction undergoes a series of color changes over time. A precipitate collects at the bottom of the tube, which is contemplated to contain the triglyceride product having at least one oleic acyl moiety of FIG. 1, in which the $R^1$, $R^2$, $R^3$, and $R^4$ groups are at least essentially those of the reactant oil and the $R^5$, $R^6$, and $R^7$ groups are assigned as shown in Table 3.

Example 32

Methyl Oleate with Lactone Modification 1 g. $Mn^{+3}$ acetyl acetonate and 4 g. of acetic acid are mixed in a test tube. 1 g. of methyl oleate is added. The tube is heated and allowed to cool following reaction. The reaction undergoes a series of color changes over time. A precipitate collects at the bottom of the vessel, which is contemplated to contain the modified methyl oleate product having at least one oleic acyl moiety of FIG. 1, in which the $R^1$, $R^2$, $R^3$, and $R^4$ groups are at least essentially those of the reactant oleate and the $R^5$, $R^6$, and $R^7$ groups are assigned as shown in Table 3.

Example 33

High Oleic Canola Oil with Dihydrofuran Modification

High oleic canola oil and acetyl acetonate (pentane-2,5-dione) are reacted with $Mn^{+3}$ acetyl acetonate as shown in FIG. 3, substituting the highest-numbered site of ethylenic unsaturation on a oleyl acyl moiety of the canola oil with a dihydrofuran fused ring. This reaction is contemplated to contain the triglyceride product having at least one oleic acyl moiety of FIG. 3, in which the $R^1$, $R^2$, $R^3$, and $R^4$ groups are at least essentially those of the reactant oil and the $R^5$, $R^6$, and $R^7$ groups are assigned as shown in Table 3.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for modifying ethylenic unsaturation in a triglyceride, comprising: providing a triglyceride having at least one fatty acyl moiety with a site of unsaturation, the triglyceride having the structure:

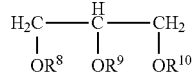

in which $R^8$, $R^9$ and $R^{10}$ are independently fatty acyl moieties, with the restriction that at least one of $R^8$, $R^9$ and $R^{10}$ is an ethylenically unsaturated fatty acyl moiety having at least one site of unsaturation available for ketone substitution; and reacting the triglyceride with a ketone, forming a dihydrofuran ring on said at least one site of unsaturation.

2. The method of claim 1, in which at least one of $R^8$, $R^9$ and $R^{10}$ is palmitoleic acyl, oleic acyl, linoleic acyl, linolenic acyl, alpha-eleostearic acyl, ricinoleic acyl, gadoleic acyl, arachidonic acyl, cetoleic acyl, or erucic acyl.

3. The method of claim 1, in which $R^8$, $R^9$ and $R^{10}$ are independently palmitoleic acyl, oleic acyl, linoleic acyl, or linolenic acyl.

4. The method of claim 1, in which the triglyceride comprises soybean oil triglyceride, partially hydrogenated soybean oil triglyceride, canola oil triglyceride, high oleic canola oil triglyceride, cottonseed oil triglyceride, rapeseed oil triglyceride, palm oil triglyceride, triglyceride of palm oil fractions, corn oil triglycerides, triglycerides made from distilled tall oil, partially hydrogenated forms of any of the above oil triglycerides, or a combination of two or more of these.

5. The method of claim 1, in which the reaction is carried out in the presence of a metal ion.

6. The method of claim 1, in which the reaction is carried out in the presence of a metal ion comprising Mn, V, or Ce.

7. The method of claim 1, in which the reaction is carried out in the presence of $Mn^{+3}$.

8. The method of claim 1, in which the reaction is carried out in the presence of manganese (III) acetylacetonate.

9. The method of claim 1, in which the reaction is carried out in the presence of an electron acceptor.

10. A method for modifying ethylenic unsaturation in a triglyceride, comprising: providing a triglyceride having at least one fatty acyl moiety with a site of unsaturation, the triglyceride having the structure:

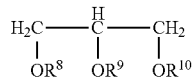

in which $R^8$, $R^9$ and $R^{10}$ are independently fatty acyl moieties, with the restriction that at least one of $R^8$, $R^9$ and $R^{10}$ is an ethylenically unsaturated fatty acyl moiety having at least one site of unsaturation available for substitution by a ketone reactant; and reacting the triglyceride with the ketone reactant, forming a dihydrofuran ring on said at least one site of unsaturation.

11. The method of claim 10, in which at least one of $R^8$, $R^9$ and $R^{10}$ is palmitoleic acyl, oleic acyl, linoleic acyl, linolenic acyl, alpha-eleostearic acyl, ricinoleic acyl, gadoleic acyl, arachidonic acyl, cetoleic acyl, or erucic acyl.

12. The method of claim 10, in which $R^8$, $R^9$ and $R^{10}$ are independently palmitoleic acyl, oleic acyl, linoleic acyl, or linolenic acyl.

13. The method of claim 10, in which the triglyceride comprises soybean oil triglyceride, canola oil triglyceride, high oleic canola oil triglyceride, cottonseed oil triglyceride, rapeseed oil triglyceride, palm oil triglyceride, triglyceride of palm oil fractions, corn oil triglycerides, triglycerides made from distilled tall oil, partially hydrogenated forms of any of the above oil triglycerides, or a combination of two or more of these.

14. The method of claim 10, in which the ketone comprises pentane-2,4-dione, diacetone alcohol, diisobutyl ketone, or a combination of two or more of these.

15. The method of claim 10, in which the ketone comprises pentane-2,4-dione, hexane-2,5-dione, diacetyl, or a combination of two or more of these.

16. The method of claim 10, in which the reaction is carried out in the presence of a metal ion.

17. The method of claim 10, in which the reaction is carried out in the presence of a metal ion comprising Mn, V, or Ce.

18. The method of claim 10, in which the reaction is carried out in the presence of $Mn^3$.

19. The method of claim 10, in which the reaction is carried out in the presence of manganese (III) acetylacetonate.

20. The method of claim 10, in which the reaction is carried out in the presence of an electron acceptor.

21. The method of claim 10, in which a ketone-substituted 2,3-dihydrofuran moiety is formed on at least one site of unsaturation.

22. A method for modifying ethylenic unsaturation in a triglyceride, comprising: providing a triglyceride having at least one fatty acyl moiety with a site of unsaturation, the triglyceride having the structure:

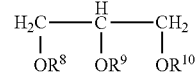

in which $R^8$, $R^9$ and $R^{10}$ are independently fatty acyl moieties, with the restriction that at least one of $R^8$, $R^9$ and $R^{10}$ is an ethylenically unsaturated fatty acyl moiety having at least one site of unsaturation available for lactone or ketone substitution; and carrying out a reaction selected from: reacting the triglyceride with a carboxylic acid having at least two carbon atoms in the presence of manganese (III) acetylacetonate, forming a lactone on said at least one site of unsaturation; or reacting the triglyceride with a ketone and a carboxylic acid having at least two carbon atoms in the presence of manganese (III) acetylacetonate, forming ketone and carboxylate pendant moieties on said at least one site of unsaturation.

23. The method of claim 22, in which at least one of $R^8$, $R^9$ and $R^{10}$ is palmitoleic acyl, oleic acyl, linoleic acyl, linolenic acyl, alpha-eleostearic acyl, ricinoleic acyl, gadoleic acyl, arachidonic acyl, cetoleic acyl, or erucic acyl.

24. The method of claim 22, in which $R^8$, $R^9$ and $R^{10}$ are independently palmitoleic acyl, oleic acyl, linoleic acyl, or linolenic acyl.

25. The method of claim 22, in which the triglyceride comprises soybean oil triglyceride, partially hydrogenated soybean oil triglyceride, canola oil triglyceride, high oleic canola oil triglyceride, cottonseed oil triglyceride, rapeseed oil triglyceride, palm oil triglyceride, triglyceride of palm oil fractions, corn oil triglyceride, triglyceride made from distilled tall oil, partially hydrogenated forms of any of the above oil triglycerides, or a combination of two or more of these.

26. The method of claim 22, in which the triglyceride is reacted with the carboxylic acid.

27. The method of claim 26, in which the carboxylic acid comprises acetic acid, propanoic acid, butanoic acid, pentanoic acid, or hexanoic acid or a combination of two or more of these.

28. The method of claim 26, in which the carboxylic acid comprises acetic acid.

29. The method of claim 26, in which the triglyceride is reacted with the ketone.

30. The method of claim 8, in which the ketone comprises acetone.

* * * * *